United States Patent

Soukal

[11] Patent Number: 6,035,328
[45] Date of Patent: Mar. 7, 2000

[54] MEDICAL THERAPEUTIC AND/OR DIAGNOSTIC SYSTEM

[75] Inventor: Peter Soukal, Schwarzenbruck, Germany

[73] Assignee: Siemens Aktiengesellschaft, Munich, Germany

[21] Appl. No.: 09/024,774

[22] Filed: Feb. 17, 1998

[30] Foreign Application Priority Data

Feb. 21, 1997 [DE] Germany .......................... 197 07 026

[51] Int. Cl.⁷ .................................................. G06F 13/00
[52] U.S. Cl. .......................................... 709/217; 600/300
[58] Field of Search ................................... 709/200, 201, 709/203, 217, 218, 219; 600/300, 301

[56] References Cited

U.S. PATENT DOCUMENTS 5,715,823  2/1998  Wood et al. ............................. 600/437
5,913,197  6/1999  Kameda ....................................... 705/3

OTHER PUBLICATIONS

"A Workstation for Biomedical Applications: Network Enhancement," Drakulic et al., Proc. of the Ninth Annual Conf. of the IEEE Eng. in Medicine and Biology Soc., Nov. 13–16, 1987, Boston, Massachusetts, vol. 1 (1987), pp. 219–220.

"Client/Server in der Labordatenverarbeitung," Riethmüller, BioTech, vol. 8, No. 5 (1996), pp. 47–49.

"Application of Modern Computer Technology to the Design of a Family of Ultrasonic Diagnostic Systems," Trukhanov et al., Biomedical Engineering, vol. 30, No. 1 (1996), pp. 30–36.

"Cadans–Design and Implementation of a Data Network for Cardiology—A Progress Report," Meester et al., Proc. Computers in Cadiology, Sep. 25–28, 1988, Washington DC.

*Primary Examiner*—Moustafa M. Meky
*Attorney, Agent, or Firm*—Hill & Simpson

[57] ABSTRACT

In a medical therapeutic and/or diagnostic system with at least one operating unit and one control unit communicating therewith, within the framework of the communications operation, at least a part of the operating and/or processing data necessary for operating the system via the operating unit is transferred from the control unit to the operating unit as needed.

14 Claims, 1 Drawing Sheet

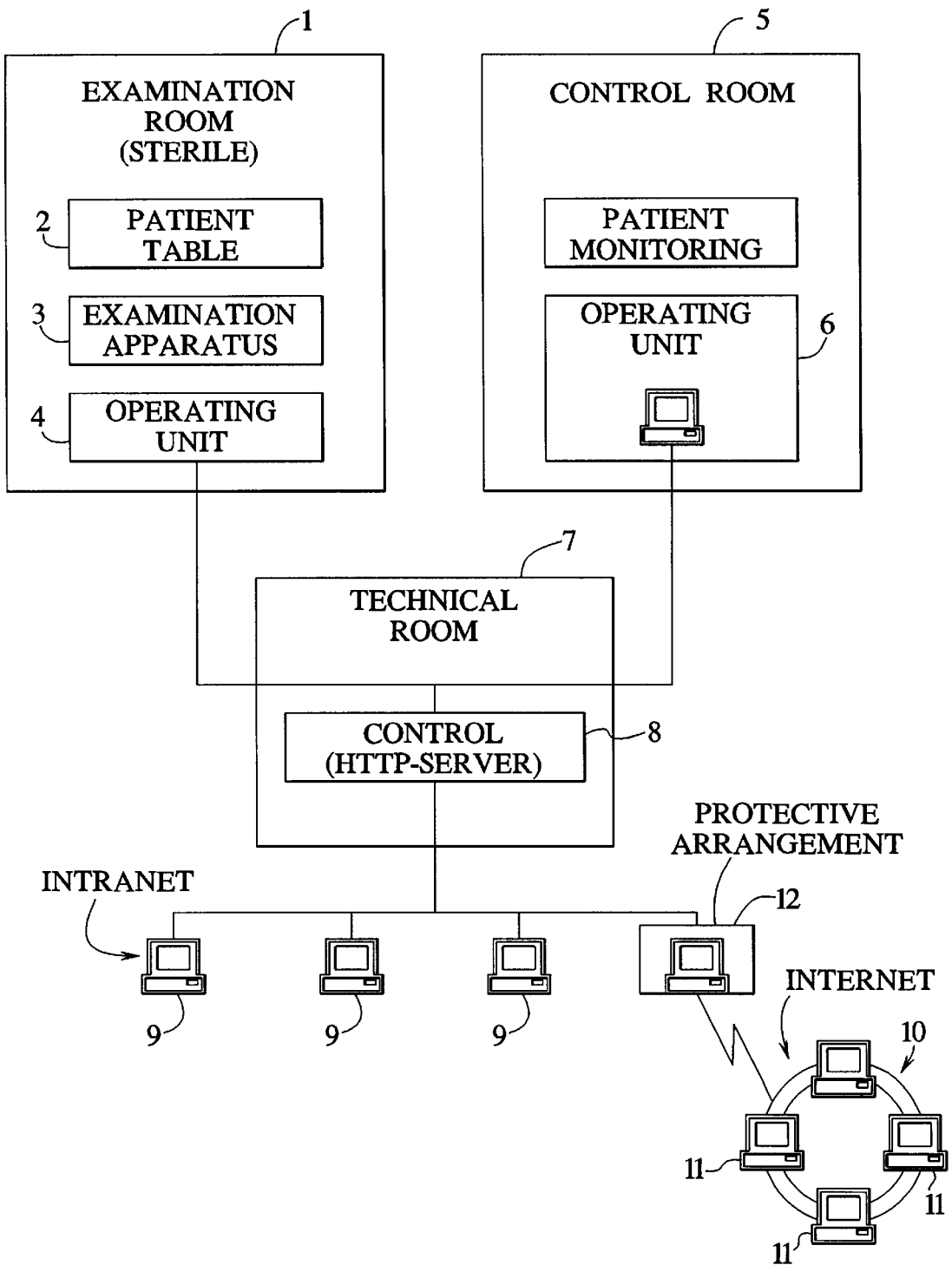

MEDICAL THERAPEUTIC AND/OR DIAGNOSTIC SYSTEM

BACKGROUND OF THE INVENTION

1. Field of the Invention

The present invention is directed to a medical therapeutic and/or diagnostic system with at least one operating means with allocated computing means and control means communicating therewith for controlling the operation of the system.

2. Description of the Prior Art

Therapeutic and/or diagnostic systems of the above type, for example an X-ray system, a system for shock wave processing or the like, have several operating units as a rule, with one being arranged near the patient and thus necessarily spatially separated from control means with which it exchanges control and display data. Thus, each operating means has computing means wherein a special software is filed which is directed to the respective medical-technical application for which it has been developed. This special software is provided in each of the operating means, since each of these operating means works quasi-"independently." Besides the inflexibility of this system, a further disadvantage is that to modify the stored software, the modification must be recorded individually for each operating means, which is cumbersome and time-consuming.

SUMMARY OF THE INVENTION

An object of the present invention is to provide a system of the type initially described wherein the aforementioned disadvantages are eliminated.

The above object is achieved in a medical therapeutic and/or diagnostic system of the type initially described wherein the operating means and the control means are designed for a communications operation wherein at least a part of the operating and/or processing data necessary to operate the system via the operating means is transferred from the control means to the operating means as needed.

In the inventive system, in contrast to known systems, at least a part of the operating and/or processing data previously stored in the computing unit of the operating means, i.e., the system's specific technical software, is not stored there anymore, but rather is only implemented in the control means, which delivers the software to the operating means only as needed, such as in the startup of the operating means or the like. The control means acts like a quasi-server. This imparts the considerable advantage that—since the necessary software is managed centrally—this must be recorded only once when a modification is made, the software that is in fact recent then being transferred automatically to the respective operating feature. This represents a considerable simplification, especially for a multi-user application.

In an embodiment of the invention the control means is designed for communication with at least one more external operating means and for a corresponding exchange of data. Indeed, it has been shown that existing systems are not always flexible enough in their operability; that is, a limitation of the operability to only the operating means provided at the system side is occasionally too rigid. In this embodiment of the invention, it is possible to operate the system from an external operating means and to establish corresponding working parameters without working immediately at the spot of the operating means at the system side. It is especially suitable if the control means and the other external operating means are connected to each other by the formation of a network (via intranet).

A more significant disadvantage of existing systems is that the communication within the system takes place in a system-specific language unique to the manufacturer. That is, the communication does not ensue on the basis of a standard protocol, but on the basis of a self-defined language. This is sometimes a disadvantage in view of the inventively provided flexible communication, since corresponding components would have to be provided as a result of communication. To remedy this, in a further embodiment of the invention the communication ensues on he basis of an HTTP-protocol. The use of this standard language allows the possibility of using simple standard components as well as a standard software, since a standardized protocol is inventively used. The computing means of the internal operating means at the system side and/or of the external operating means can then inventively comprise a standard computer with a corresponding browser, which simplifies the entire system configuration. The communications operation can be inventively selected via the computer, such that the data transfer ensues automatically upon the startup of the operating means or shortly thereafter, which is especially guaranteed when a corresponding network-PC is used as computing means. This network-PC establishes contact independently with the control means, which acts subsequently as an HTTP-server, over the HTTP protocol after a completed booting.

In order to allow external operability of a corresponding operating means outside the intranet in addition to the operability of the system within the intranet, in another embodiment of the invention means allowing access to an external communication network, especially to the Internet, are allocated to the control means. The Internet, as the most well-known worldwide data transfer network, likewise functions on the basis of an HTTP-protocol, for which reason a communication between the system and an external operating means is possible over the Internet. In this manner, the possibility of a world-wide remote operability is realized. Besides the actual system operation, of course system maintenance is also provided, such as via an external operating means in the intranet or the Internet New software and the like can also be run. For access to the external communications network one or more external operating means, i.e., the computers thereof. Preferably, operating means already integrated in the Internet are used, as, for example, the standard PC.

In a further embodiment the control means and the operating means at the system side and/or external operating means are designed for communication using the CGI technology and/or Java technology. The CGI technology (Coment Gateway Interface) allows the control means acting as server to react to requests and to prompt actions and outputs. The employment of Java technology, by means of which it is possible to create Java-applets, has the advantage that the performance demands on the control unit are therefore lower, since the computing capacity for the operation of Java-applet is obtained from the operating unit itself, to which this computing capacity is transferred from the control means. That is, the execution of the program ensues directly at the operating means itself and not within the control means.

In addition, the invention is directed to a method for operating a medical therapeutic and/or diagnostic system with at least one operating means at the system side and one external operating means, each of which comprises a computing means, and a control means communicating therewith to control the operation of the system, wherein the control means and all the operating means communicate with each other in a unified language and the operation of the control means, and thus the overall system, is possible via each of the operating means.

In an embodiment of the inventive method, within the framework of the communication, at least a part of the operating and/or processing data necessary for operation via the respective operating means is transferred from the control means to the respective operating means as needed. The control means and the operating means can therein communicate with each other on the basis of an HTTP protocol.

DESCRIPTION OF THE DRAWINGS

FIG. 1 shows an example of the architecture of an inventive medical therapeutic and/or diagnostic system including an external operating option.

DESCRIPTION OF THE PREFERRED EMBODIMENTS

The inventive system is used (in part) in an examination room 1, which can be sterile and in which a patient table 2, an examination device 3 and an operating unit 4 for local operation can be provided, among other installations, and in a control room 5 in which patient monitoring takes place and in which another operating unit 6 is provided, and in a technical room 7 in which the control unit 8 is located. The use of the term "technical room" means that the control unit 8 is separated at least locally from the remaining means as an independent device. The communication between the operating units 4 and 6 and the control unit 8 ensues via an HTTP protocol, so that the control unit 8 acts as an HTTP-server, which places the necessary operating and/or processing data, i.e. the respective software, at the operating unit side, at one's disposal as needed. This occurs preferably using of the Java technology, in the framework of which, in page call-up, a computer-platform-independent program created in the Java programming language and embedded in HTML pages is loaded by a browser at the operating unit side and is then exported. The advantage of this technology lies in relieving the control unit 8, since the export of the respective program loaded in the described manner ensues at the operating unit of the viewer.

As can be further seen from the FIGURE, the control unit 8 is connected to several external operating units 9, wherein communication also takes place via an HTTP protocol. The operating unit 9 and the control unit 8—also connected to the other operating units 4 and 6—are integrated in a self-contained (i.e., non-public) intranet. The operating unit 9, it can be a standard network PC run on software according to standard, since the communication takes place via the standardized HTTP protocol, for which corresponding software exists. It is likewise possible to carry out a system operation using the operating unit 9.

In order to carry out an operation from an operating unit external to the intranet as well, one of the operating units 9 is provided with a means for accessing a public network 10, such as the Internet, via which the control unit 8, and with it the system, can likewise be accessed from another external operating means 11 via the corresponding operating unit 9. In this way, a semi-unlimited world-wide operability is realized. Only a protective arrangement 12 is necessary for preventing unauthorized access.

Although modifications and changes may be suggested by those skilled in the art, it is the intention of the inventor to embody within the patent warranted hereon all changes and modifications as reasonably and properly come within the scope of his contribution to the art.

I claim as my invention:

1. A medical system comprising:

medical procedure means for performing a medical procedure in a medical procedure environment;

on-site operating means in said medical procedure environment for operating said medical procedure means;

control means in communication with said operating means for storing data comprising at least one of operating data and processing data for use in operating said medical procedure means;

an internal communication path connected to said control means;

off-site operating means disposed outside of said medical procedure environment and connected to said internal communication path, for exchanging data with said control means via said internal communication path and for allowing operation of said medical procedure means via said internal communication path and said control means;

accessing means for accessing an external communication path and communicating with said control means for exchanging data with said external communication path and for allowing operation of said medical procedure means by said off-site operating means via said external communication path and said control means; and said control means comprising means for storing data comprising at least one of operating data and processing data employable for operating said medical procedure means and for transferring said data to at least one operating means among said on-site operating means and said off-site operating means only as needed by said at least one operating means.

2. A medical system as claimed in claim 1, wherein said off-site operating mens includes said accessing means.

3. A medical system as claimed in claim 1 wherein said medical procedure environment comprises an examination room and a control room, and wherein said on-site operating means comprises a first operating unit disposed in said examination room and a second operating unit disposed in said control room, each of said first and second operating units being connected to said control means.

4. A medical system as claimed in claim 1 wherein said internal communication path comprises a non-public network.

5. A medical system as claimed in claim 1 wherein said on-site operating means, said control means and said off-site operating means communicate with each other via an HTTP protocol.

6. A medical system as claimed in claim 5 wherein each of said on-site operating means and said off-site operating means comprises a standard personal computer.

7. A medical system as claimed in claim 1 wherein said at least one operating means comprises means for initiating a start-up prior to performing said medical procedure, and wherein said control means comprises means for transferring said data automatically at a time coinciding with said start-up.

8. A medical system as claimed in claim 1, wherein said off-site operating means comprises a plurality of individual operating units, each of said operating units including mens for accessing said external communication path enabling operation of said medical procedure means by said external off-site operating means via said second communication path, said off-site operating means, said internal communication path and said control means.

9. A medical system as claimed in claim 1 wherein said on-site operating means, said control means and said off-site operating means comprise means for communicating each other with technology selected from the group consisting of CGI technology and Java technology.

10. A medical system comprising:

medical procedure means for performing a medical procedure in a medical procedure environment;

on-site operating means in said medical procedure environment for operating said medical procedure means;

off-site operating means disposed outside of said medical procedure environment for operating said medical procedure means, said off-site operating means including means for accessing an external communication network; and control means communicating in a unified programming language with each of said on-site operating means and said off-site operating means for allowing operation of said medical procedure means by any of said on-site operating means and said off-site operating means, and via said external communication network.

11. A medical system as claimed in claim 10 wherein said control means further comprises means for temporarily transferring data in said unified programming language for operating said medical procedure means to any of said on-site operating means, said off-site operating means, and via said external communication network.

12. A medical system as claimed in claim 10 wherein said unified programming language comprises an HTTP protocol.

13. A method for operating a medical system comprising:

disposing an apparatus for conducting a medical procedure in a medical procedure environment;

disposing at least one on-site operating unit in said medical procedure environment;

disposing at least one offsite operating unit outside of said medical procedure environment;

providing access to an external communication network via said at least one off-site operating unit;

providing a control unit in communication with each on-site operating unit, each off-site operating unit and said external communication network and communicating between each on-site operating unit, each off-site operating unit and said external communication network with a unified programming language;

operating said medical procedure apparatus via any on-site operating unit, any off-site operating unit and via said external communication network including, before operating said medical procedure apparatus, transferring data for operating said medical procedure apparatus from said control unit to said at least one on-site operating unit, said at least one off-site operating unit or to said external communication network.

14. A method as claimed in claim 13 wherein the step of communicating with a unified programming language comprises communicating with an HTTP protocol.

* * * * *